(12) United States Patent
Rasnik

(10) Patent No.: US 10,378,996 B2
(45) Date of Patent: Aug. 13, 2019

(54) METHODS AND APPARATUS FOR DETERMINING GEOMETRIC PROPERTIES OF OPTICAL FIBER PREFORMS

(71) Applicant: Heraeus Quartz North America LLC, Buford, GA (US)

(72) Inventor: Ivan Rasnik, Decatur, GA (US)

(73) Assignee: Heraeus Quartz North America LLC, Buford, GA (US)

( * ) Notice: Subject to any disclaimer, the term of this patent is extended or adjusted under 35 U.S.C. 154(b) by 0 days.

(21) Appl. No.: 15/502,705

(22) PCT Filed: Aug. 8, 2014

(86) PCT No.: PCT/US2014/050368
§ 371 (c)(1),
(2) Date: Feb. 8, 2017

(87) PCT Pub. No.: WO2016/022151
PCT Pub. Date: Feb. 11, 2016

(65) Prior Publication Data
US 2017/0234769 A1  Aug. 17, 2017

(51) Int. Cl.
*G01N 21/41* (2006.01)
*G01M 11/00* (2006.01)
(Continued)

(52) U.S. Cl.
CPC .............. *G01M 11/37* (2013.01); *G01B 11/08* (2013.01); *G01B 11/24* (2013.01); *G01B 11/25* (2013.01);
(Continued)

(58) Field of Classification Search
CPC ....... G01B 11/00; G01B 11/02; G01B 11/105; G01B 11/08; G01B 11/12; G01N 21/412
(Continued)

(56) References Cited

U.S. PATENT DOCUMENTS 4,181,433 A * 1/1980 Marcuse .............. G01N 21/412
356/128
4,638,168 A * 1/1987 Marino .................. G01B 11/12
250/358.1
(Continued)

FOREIGN PATENT DOCUMENTS

CN        1246611 A     3/2000
CN      101298363 A    11/2008
(Continued)

OTHER PUBLICATIONS

Office Action and Search Report dated Jul. 4, 2018 in CN Application No. 201480081100.X.
(Continued)

*Primary Examiner* — Hoa Q Pham
(74) *Attorney, Agent, or Firm* — Panitch Schwarze Belisario & Nadel LLP

(57) ABSTRACT

Methods and apparatus for evaluating the geometric properties of optical fiber preforms, which methods include: providing an optical fiber preform having a longitudinal axis, an outer diameter and a circumference; providing a two-dimensional pattern having a length parallel to the longitudinal axis of the preform and a width greater than the outer diameter of the preform; providing an image capturing device disposed such that the preform is aligned between the pattern and the image capturing device; rotating the preform about its longitudinal axis and acquiring a first plurality of images of the pattern viewed through the preform at at least two different points along the circumference of the preform; and determining at least one geometric property of the preform from the first plurality of images.

20 Claims, 4 Drawing Sheets

(51) Int. Cl.
*G01B 11/08* (2006.01)
*G01B 11/24* (2006.01)
*G01B 11/25* (2006.01)
*G01N 21/95* (2006.01)
*G01N 21/958* (2006.01)
*G06T 7/60* (2017.01)

(52) U.S. Cl.
CPC ........... *G01N 21/412* (2013.01); *G01N 21/95* (2013.01); *G01N 21/958* (2013.01); *G01N 2021/9511* (2013.01); *G06T 7/60* (2013.01)

(58) Field of Classification Search
USPC .................. 356/73.1, 426–428, 625–635
See application file for complete search history.

(56) References Cited

U.S. PATENT DOCUMENTS

| | | | |
|---|---|---|---|
| 5,172,421 A * | 12/1992 | Nakamura | G01M 11/35 250/559.08 |
| 6,025,906 A | 2/2000 | Hepburn et al. | |
| 6,538,755 B1 | 3/2003 | Propst, Jr. | |
| 6,611,321 B1 | 8/2003 | Sasaki | |
| 2002/0180958 A1* | 12/2002 | Sasaki | G01M 11/088 356/128 |
| 2008/0198389 A1 | 8/2008 | Yoo et al. | |

FOREIGN PATENT DOCUMENTS

| | | |
|---|---|---|
| CN | 104067605 A | 9/2014 |
| EP | 0905477 A2 | 3/1999 |
| JP | 2000162152 A | 6/2000 |
| JP | 2005275447 A | 10/2005 |
| JP | 2005346665 A | 12/2005 |
| JP | 2008273798 A | 11/2008 |
| JP | 2013168119 A | 8/2013 |

OTHER PUBLICATIONS

Office Action dated Feb. 5, 2018 in JP Application No. 2017506966.
Office Action dated Oct. 29, 2018 in JP Application No. 2017506966.
Office Action dated Sep. 19, 2018 in KR Application No. 10-2017-7005308.
Int'l Search Report dated May 8, 2015 in Int'l Application No. PCT/US2014/050368.
Int'l Preliminary Report on Patentability and Written Opinion dated Feb. 14, 2017 in Int'l Application No. PCT/US2014/050368.
Office Action dated Feb. 16, 2019 in KR Application No. 10-2017-7005308.
Office Action dated Mar. 14, 2019 in CN Application No. 201480081100.

* cited by examiner

METHODS AND APPARATUS FOR DETERMINING GEOMETRIC PROPERTIES OF OPTICAL FIBER PREFORMS

CROSS-REFERENCE TO RELATED APPLICATION

This application is a Section 371 of International Application No. PCT/US2014/050368, filed Aug. 8, 2014, which was published in the English language on Feb. 11, 2016, under International Publication No. WO 2016/022151 A1, the disclosure of which is incorporated herein by reference.

TECHNICAL FIELD

The invention is directed to methods and apparatus for determining geometric properties of optical fibers and optical fiber preforms in a robust, inexpensive, and high speed manner such that analysis can be carried out in a production environment with a high level of accuracy and precision.

BACKGROUND

An optical fiber typically comprises a core portion and one or more cladding layers and permits the propagation of light rays along the core portion. For this reason, if two optical fibers are connected to one another, the cores of these two optical fibers should be precisely aligned. If the external shapes of two optical fibers coincide with one another, but either or both of the cores have eccentricity, the connection loss increases due to the discrepancy between the positions of these cores. For this reason, the preform as a starting material to be drawn into an optical fiber should comprise a core portion with minimal eccentricity. In the production of an optical fiber and the management thereof, it is very important to inspect an optical fiber preform as a starting material and to thus select an optical fiber preform comprising a core portion having low eccentricity from the foregoing standpoint. Additional geometric properties, in addition to eccentricity, are also important, including the outer diameter of the core and cladding, as well as any ovality.

While such properties could be visually inspected and measured at a given cross-section of an optical fiber preform, such a methodology is cumbersome and slow, requiring taking multiple cross-sections of a fiber preform along its length, and not at all suited to commercial production of fiber preforms. Moreover, as such methodologies would require taking multiple cross-sections of a preform along its length, they would effectively destroy the preform. Alternatively, an optical fiber preform could be immersed in a refractive index matching oil and scanned with a laser beam to determine its refractive index and geometric properties but the necessity and the cost of cleaning the preforms after oil immersion are not desirable for the low cost commercial production of optical preforms. The invention provides a low cost method for measuring the geometrical properties of the fiber preform in air and in a non-destructive manner and furthermore allows for additional cost reduction by eliminating the cost of fiber draw from parts of the preforms which do not satisfy the geometrical specifications.

Accordingly, methodologies for determining geometric properties of optical fiber preforms in commercial production must be able to quickly provide such determinations without damaging or altering the preform. Currently, no such low cost, robust and accurate inspection and measurement methodologies exist. Previous methodologies to determine the geometrical properties of optical fiber preforms require polarized light, or complex, costly and difficult to handle operations such as immersion in a material (e.g., a refractive index matching oil) having the same index or refraction as the cladding material of the preform. These alternative methods have errors related to sensitivity to local light environment and require handling and operation not compatible with low cost production inspection and measurement process.

SUMMARY

The invention is directed, in general, to fiber optics, and more specifically, methods and apparatus for measuring one or more geometric properties of optical fiber preforms, as well as drawn optical fibers. Various embodiments of the invention can provide quick, accurate, precise, robust and repeatable measurement of various geometric characteristics, without the need for matching oils, or polarized light or other features that result in a sensitivity to local light levels. Geometric properties which can be determined in accordance with the methods and apparatus of the various embodiments of the invention include the diameters, ovalities, clad-to-core or "D/d" ratio, and eccentricities of the preform core and cladding, as well as overall preform bow.

One embodiment of the invention includes a method comprising: (a) providing an optical fiber preform having a longitudinal axis, an outer diameter and a circumference; (b) providing a two-dimensional pattern having a length parallel to the longitudinal axis of the preform and a width greater than the outer diameter of the preform; (c) providing an image capturing device disposed such that the preform is aligned between the pattern and the image capturing device; (d) rotating the preform about its longitudinal axis and acquiring a first plurality of images of the pattern viewed through the preform at at least two different points along the circumference of the preform; and (e) determining at least one geometric property of the preform from the first plurality of images.

Another embodiment of the invention includes a method comprising: (a) providing an optical fiber preform having a longitudinal axis, an outer diameter, a circumference, and comprising at least two cylindrical layers of glass having different indices of refraction; (b) providing a two-dimensional pattern having a length parallel to the longitudinal axis of the preform and a width greater than the outer diameter of the preform, wherein the two-dimensional pattern comprises alternating dark and bright lines or fringes (the terms "lines" and "fringes" are used synonymously herein in reference to two-dimensional patterns), arranged periodically, and positioned at a non-perpendicular angle relative to the longitudinal axis of the preform, wherein the two-dimensional pattern is illuminated, wherein the alternating dark and bright lines or fringes each have a thickness; (c) providing digital camera (which may have an internal lens, or an external lens) disposed such that the preform is aligned between the pattern and the digital camera; (d) rotating the preform about its longitudinal axis and acquiring a first plurality of images of the pattern viewed through the preform at at least ten different points along the circumference of the preform; (e) moving the preform in the direction of its longitudinal axis, and rotating the preform about its longitudinal axis and acquiring a second plurality of images of the pattern viewed through the preform at at least ten different points along the circumference of the preform at a different location along its length than the first plurality of images; and (0 determining the diameter, ovality and eccentricity of each of the at least two cylindrical layers of the preform from the first plurality and second plurality of images, wherein the thickness of each fringe of the pattern in the first and second plurality of images captured by the digital camera is at least more than one pixel, wherein the determination comprises evaluating perturbations of the two-dimensional pattern in the first plurality of images and second plurality of images to determine relative spatial position of an edge between the at least two cylindrical layers at two different positions along the longitudinal axis of the preform; and wherein evaluating the perturbations of the two-dimensional pattern in each of the first plurality of images and the second plurality of images to determine the relative spatial position of the edge comprises an analysis of image pixels comprising image erosion noise reduction, standard deviation filtering, image projection averaging and magnification compensation.

Another embodiment of the invention includes an apparatus for determining a geometric property of an optical fiber preform, the preform having a longitudinal axis and an outer diameter, the apparatus comprising: an image capturing device; a two-dimensional pattern having a length parallel to the longitudinal axis of the preform and a width greater than the outer diameter of the preform; a support configured to position the preform in alignment between the image capturing device and the two-dimensional pattern, such that the two dimensional pattern extends length-wise in the direction of the longitudinal axis of the preform and the beyond the outer diameter of the preform in each direction when viewed from the image capturing device; and a driver configured to rotate the preform about its longitudinal axis in the support.

Other aspects, features and advantages will be apparent from the following disclosure, including the detailed description, preferred embodiments, and the appended claims.

BRIEF DESCRIPTION OF THE DRAWINGS

The foregoing summary, as well as the following detailed description of preferred embodiments of the invention, will be better understood when read in conjunction with the appended drawings. For purposes of illustration the invention, there are shown in the drawings embodiments which are presently preferred. It should be understood, however, that the invention is not limited to the precise arrangements and instrumentalities shown.

In the drawings.

DETAILED DESCRIPTION

Figure 1:
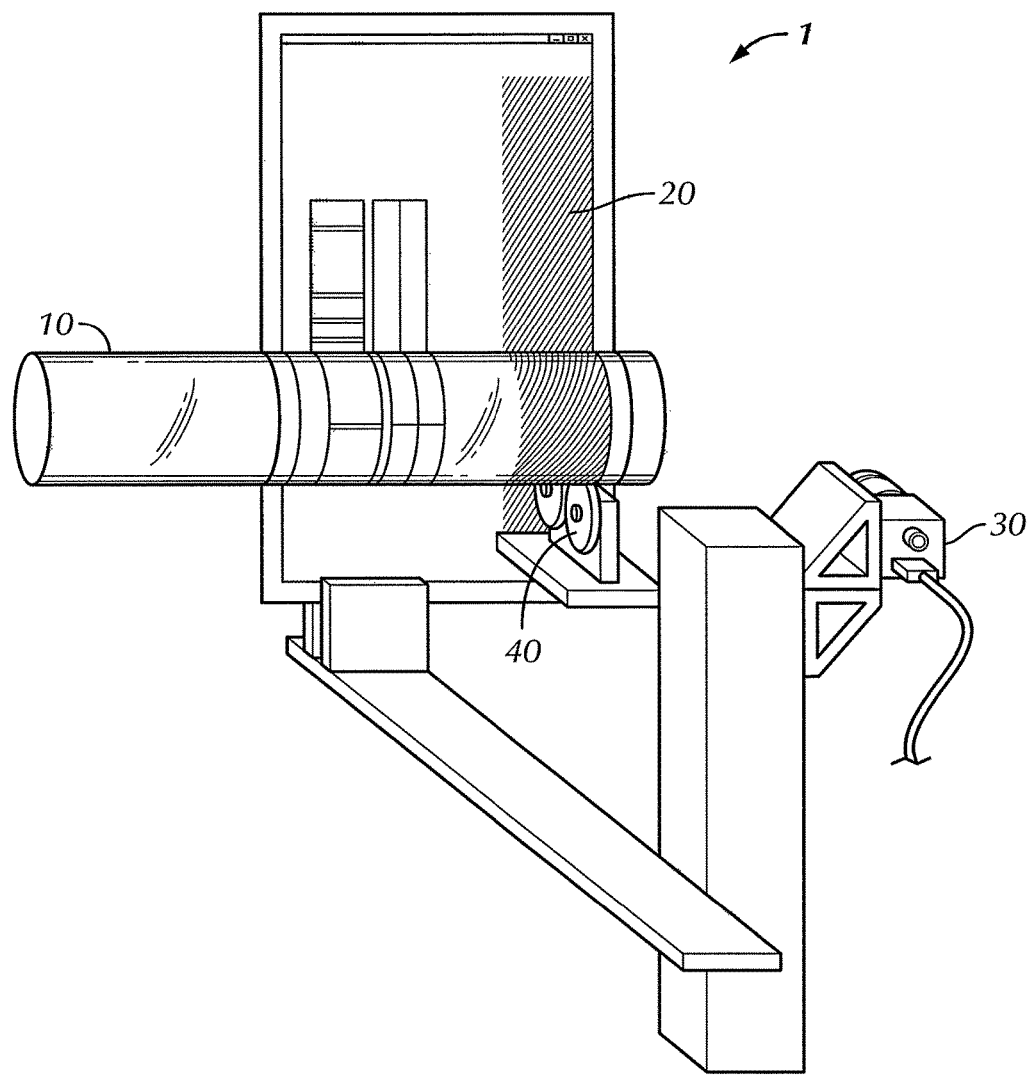
FIG. 1 is a schematic view of an apparatus in accordance with one embodiment of the invention.

As used herein, the singular terms "a" and "the" are synonymous and used interchangeably with "one or more" and "at least one," unless the language and/or context clearly indicates otherwise. Accordingly, for example, reference to "a preform" or "the preform" herein or in the appended claims can refer to a single preform or more than one preform. Additionally, all numerical values, unless otherwise specifically noted, are understood to be modified by the word "about."

For simplicity and clarity of illustration, elements in the figures are not necessarily to scale, and the same reference numbers in different figures denote the same elements.

Certain terminology, when used in the following description, is for convenience only and is not limiting, including words such as "right", "left", "lower", and "upper," which may designate directions in the drawing to which reference is made, and words such as "inwardly" and "outwardly," which may refer to direction toward and away from, respectively, the geometric center of the object described and designated parts thereof. The terminology includes the words above specifically mentioned, derivatives thereof and words of similar import.

Various embodiments of the invention include apparatus for determining one or more geometric properties of an optical fiber preform. While the various embodiments of the invention described herein refer to apparatus and methods for determining one or more geometric properties of an optical fiber preform, the apparatus and methods can be used for determining one or more geometric properties of drawn optical fibers by incorporating microscopy (i.e., magnification of the acquired images). The apparatus in accordance with the various embodiments of the invention can provide accurate, precise and robust geometric characterization, and can advantageously do so in a production environment at a high rate of speed. The apparatus in accordance with various embodiments of the invention include an image capturing device, a two-dimensional pattern, a support for positioning an optical fiber preform in alignment between the two-dimensional pattern and the image capturing device, and a driver configured to rotate the preform about its longitudinal axis in the support. In various embodiments of the invention, the apparatus can further include a driver configured to move the image capturing device and the two-dimensional pattern relative to the optical fiber preform in a direction along the longitudinal axis of the preform. In various embodiments of the invention, the driver configured to rotate the preform about its longitudinal axis in the support may also be configured to move the preform in a direction along its longitudinal axis relative to the two-dimensional pattern and the image capturing device.

Referring to FIG. 1, an apparatus 1 in accordance with an embodiment of the invention includes a two-dimensional pattern 20 and an image capturing device 30. In the embodiment depicted in FIG. 1, the image capturing device is a digital camera. The apparatus shown in the embodiment depicted in FIG. 1 includes a support and a driver 40 configured to rotate an optical fiber preform 10 about its longitudinal axis. The portion of the support shown in FIG. 1, positioning the right end of the optical fiber preform 10 also includes the driver configured to rotate the preform. The support and the driver may be a unitary structure or they may be separate devices. The support is structured to align the preform between the two-dimensional pattern and the image capturing device such that the images captured are of the two-dimensional pattern as viewed through the preform.

Figure 2A:
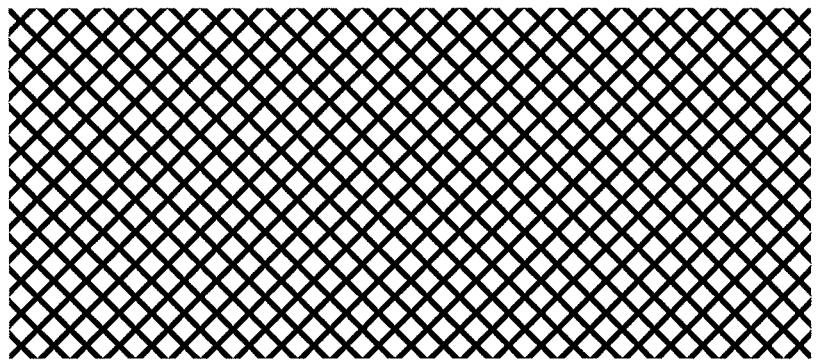
FIG. 2a is a graphical representation of a two-dimensional pattern suitable for use in accordance with various embodiments of the invention.
Figure 2B:
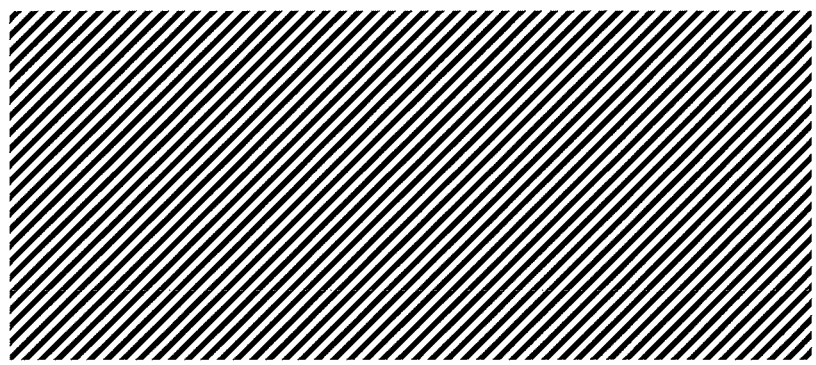
FIG. 2b is a graphical representation of another two-dimensional pattern suitable for use in accordance with various embodiments of the invention.
Figure 2C:
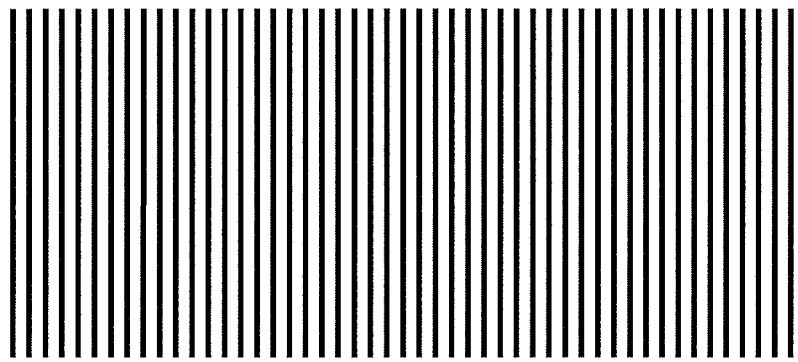
FIG. 2c is a graphical representation of another two-dimensional pattern suitable for use in accordance with various embodiments of the invention.

Apparatus in accordance with the various embodiments of the invention include a two-dimensional pattern. Any pattern which is repetitive could be used so long as it is repetitive in two dimensions. Two-dimensional patterns suitable for use in the various embodiments of the invention do not necessarily need to be complex. Suitable preferred two dimensional patterns are periodic along the length of the pattern. In this regard, the length of the pattern is considered to be the dimension in parallel with the longitudinal axis of an optical fiber preform being geometrically characterized. Various preferred patterns which may be used in embodiments of the invention can be illuminated. The source of illumination can vary, and includes, but is not limited to, any wide field illumination source, projected light, etc. In various embodiments of the invention, it is preferable that the pattern comprise two contrasting colors, more preferably a dark and a bright color, and most preferably, black and white. Referring to FIGS. 2a through 2c, examples of two-dimensional patterns suitable for use in various embodiments of the invention are shown. In FIG. 2a, a suitable two-dimensional pattern of a repeating black cross-hatch on a white background is shown. In FIG. 2b, a suitable two-dimensional pattern of repeating black lines disposed at an angle on a white background is shown. In FIG. 2c, a suitable two-dimensional pattern of repeating vertical black lines on a white background is shown. In various preferred embodiments of the invention, the two-dimensional pattern may be illuminated to improve the contrast of the colors employed in the pattern.

Figure 3:
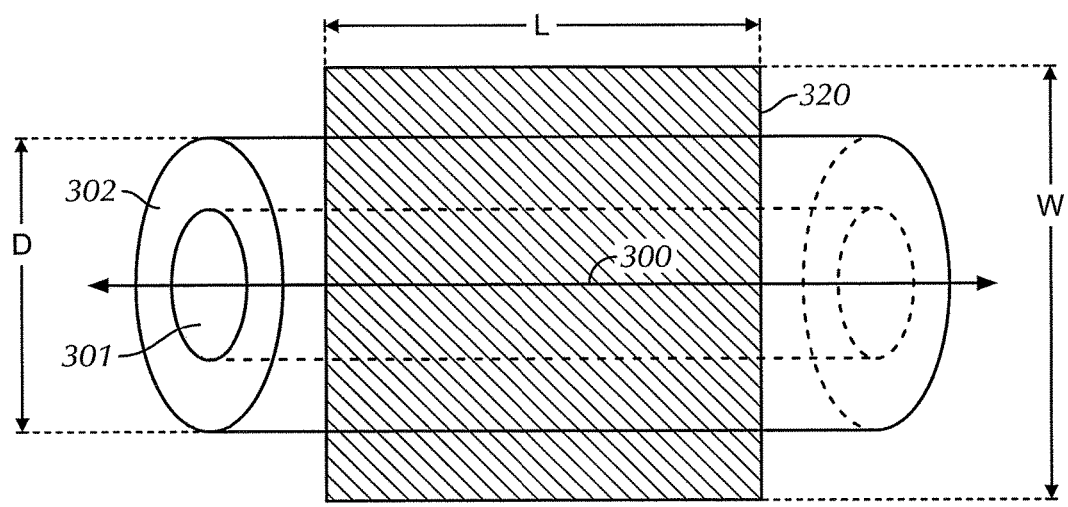
FIG. 3 is a schematic representation of an optical fiber preform in relation to a two-dimensional pattern in accordance with an embodiment of the invention.

Throughout this description, reference is made to the orientation of an optical fiber preform in relation to a two-dimensional pattern. For better understanding, reference can be made to FIG. 3. In FIG. 3, a graphical representation of an optical fiber preform disposed in front of a two-dimensional pattern is shown. An optical fiber preform is a precursor to optical fiber. Optical fiber comprises a core of a glass material surrounded by one or more cladding layers of glass material having a different index of refraction than the first (core) glass material. An optical fiber preform similarly has a core and cladding (one or more cladding layers), and can be heated and pulled or stretched to form optical fiber. In FIG. 3, an optical fiber preform 10 is shown. The optical fiber preform 10 has a longitudinal axis 300. The optical fiber preform 10 comprises a core 301 and cladding 302. The preform 10 has an outer diameter D which is the diameter of the outside of the cladding layer. A two-dimensional pattern 320 is disposed behind the preform 10. It is to be understood that additional cladding layers may be present and multiple outer or cladding diameters (e.g., $D_1$, $D_2$, $D_3$ for a three cladding layer preform) could be measured. Two-dimensional pattern 320 has a length L which spans a direction parallel to the longitudinal axis 300 of the preform 10. The width W of the two-dimensional pattern 320 spans a direction parallel to the outer diameter D of the preform 10, i.e., perpendicular to the longitudinal axis 300.

The length L of a two-dimensional pattern suitable for use in the various embodiments of the invention is not critical, but as explained in more detail herein below, the length L of the two-dimensional pattern can advantageously extend in a direction along the longitudinal axis of the optical fiber preform being characterized for multiple repetitions of the pattern. Typically, two or more repetitions of the pattern are sufficient for use in the methods according to the various embodiments of the invention. On the other hand, it is important that a two-dimensional pattern for use in the various embodiments of the invention extend beyond the outer diameter D of the optical fiber preform in its width W direction. It is important that the pattern extend in its width W direction beyond the outer diameter of the optical fiber preform so that the dimension of the outer diameter can be determined in accordance with the methods of the various embodiments of the invention.

Apparatus in accordance with the various embodiments of the invention include an image capturing device. Any image capturing device can be employed. Preferably, the image capturing device comprises a digital camera. Digital capture of image can provide fast acquisition rates advantageous for on-line, production environment inspection. In various embodiments of the invention, the apparatus includes a digital camera having an internal lens. In various embodiments of the invention, the apparatus includes a digital camera having no internal lens, and an external focusing lens disposed between the preform and the digital camera. Preferably, a digital camera for use in the various embodiments of the invention will have a large number of pixels. The more pixels present in an image captured by the digital camera, the higher the accuracy of the geometric determination as there will be more pixels encompassed within the width (thickness) of a fringe in the pattern image captured by the camera. While the operational features of any particular digital camera are not critical, the frames per second and exposure time are important in relation to the speed at which an optical fiber preform is rotated. Thus, for example, if the optical fiber preform is rotated at a speed of one rotation per second and three images are to be acquired per rotation, the digital camera must operate at a minimum of three frames per second. Additionally, exposure time should be kept short to avoid blurring.

As discussed above, two-dimensional patterns suitable for use in various preferred embodiments of the invention can be comprised of two contrasting colors, more preferably black and a bright, monochromatic color. Such single wavelength light can be provided by use of a filter. Additionally, suitable two-dimensional patterns can preferably be illuminated. In various more preferred embodiments of the invention, a two-dimensional pattern comprises alternating lines of contrasting color, even more preferably, black and a bright, monochromatic color for maximum contrast. In various preferred embodiments of the invention, a suitable two-dimensional pattern comprises alternating lines of contrasting colors disposed at an angle, not perpendicular to the longitudinal axis of an optical fiber preform. A preferred non-perpendicular angle can be 40° to 50°, and in various more preferred embodiments, is 45°. Accordingly, in certain preferred embodiments of the invention, a two-dimensional pattern comprises alternating black and white lines disposed at a 45° angle relative to the longitudinal axis of an optical fiber preform to be characterized. The lines of a two-dimensional pattern suitable for use in the various embodiments of the invention may be of any thickness. In various preferred embodiments of the invention, the thickness of the lines in a two-dimensional pattern, as measured at the imaging plane of a digital camera spans at least two pixels of the digital sensor, more preferably at least three pixels, and even more preferably, at least five pixels.

Apparatus in accordance with the various embodiments of the invention include a support and a driver configured to rotate an optical fiber preform about its longitudinal axis. A support and a driver can be combined as one structure or device, or they may be entirely separate. Any structure which is capable of stabilizing an optical fiber preform such that it is aligned between a two-dimensional pattern and an image-capturing device, and such that the preform is able to rotate about its longitudinal axis can be suitably used in the various embodiments of the invention. Any driver which can exert torque such that the preform rotates about its longitudinal axis without dislodging the preform from its supported position can be suitably used in the various embodiments of the invention, including but not limited to, for example, belts, rollers, chains, lathe mounts and similar equipment. In various embodiments of the invention, the support and/or driver may further include a device for detecting angular position of a preform relative to a designated starting position. Such detection can be accomplished, for example, by a marking on the preform and optical detection of the marking during rotation. Alternatively, a preform can be marked along its length and such detection can be carried out through the image capturing device.

Various embodiments of the invention are directed to methods of determining various geometric characteristics or properties of optical fiber preforms. Methods in accordance with the various embodiments of the invention may be carried out using apparatus according to various other embodiments of the invention.

Geometric characteristics or properties of an optical fiber preform which may be determined in accordance with the methods of the invention include the diameters, ovalities, D/d ratio, and eccentricities of the preform core and cladding, as well as overall preform bow. An optical fiber preform comprises a cylindrical core and a cladding layer surrounding the core. Thus, an optical fiber preform has a core diameter, d, and an outer diameter of the cladding layer, D (or multiple cladding layer diameters where more than one cladding layer is present). From the core diameter, d, and the outer diameter, D, a ratio of diameters, D/d can be determined. Each of the core and cladding layer of an optical fiber preform is ideally cylindrical having a circular cross-section. Deviation from a perfect circular cross-section, or varying orthogonally-measured radii, is referred to as ovality. As cylindrical forms, each of the core and cladding has a geometric center defined by their respective lengthwise axes. Deviation from a shared geometric center line between the core and cladding is referred to as eccentricity (i.e., not concentric). Overall preform bow refers to any deviation from linearity along the length of the preform.

Methods in accordance with the various embodiments of the invention include providing an optical fiber preform. Any optical fiber preform as described herein, having a longitudinal axis, an outer diameter and a circumference may be used in the methods of the invention. Methods in accordance with the various embodiments of the invention further include providing a two-dimensional pattern. Any two-dimensional pattern as described herein, having a length parallel to the longitudinal axis of the optical fiber preform and a width greater than the outer diameter of the preform may be used in the methods of the invention. Two-dimensional images described as preferred in accordance with the apparatus embodiments of the invention are preferred for use in the method embodiments of the invention as well. Methods in accordance with the various embodiments of the invention further include providing an image capturing device. Preferably, a digital camera is used in the method embodiments of the invention.

Thus, methods in accordance with various embodiments of the invention include providing an optical fiber preform, a two-dimensional pattern and an image capturing device such that the preform is aligned between the pattern and the image capturing device, whereby images captured by the image capturing device are of the pattern as viewed through the preform.

Methods in accordance with the various embodiments of the invention further include rotating the preform about its longitudinal axis and acquiring a plurality of images of the pattern viewed through the preform. A plurality of images includes at least two images of the pattern as viewed through the preform at different points along the circumference of the preform (where the two different points are not 180° apart). In other words, a plurality of images includes at least one image of the pattern viewed through the preform where a line extending from the image capturing device to the pattern, through the preform, is incident on the preform at a first point A along its circumference, and at least one image where such a line is incident on the preform at a different point along its circumference, after the preform has been rotationally moved. In various preferred embodiments of the methods according to the invention, a plurality of images includes images of the pattern viewed through the preform at at least five different points along the circumference of the preform. In various more preferred embodiments of the methods according to the invention, a plurality of images includes images of the pattern viewed through the preform at at least ten different points along the circumference of the preform. In various most preferred embodiments of the methods according to the invention, a plurality of images includes images of the pattern viewed through the preform at at least fifteen different points along the circumference of the preform.

The speed at which the preform is rotated is not critical, but may be optimized for the speed at which preforms are evaluated. Ideally, a plurality of images is obtained in one rotation of the preform. Thus, for example, if the plurality of images is selected to include images at ten different points along the circumference of the preform, a single rotation period should be ten times as long as it takes for the image capturing device to capture an image. For example, when a digital camera is used, and ten different images along the circumference are to be obtained, the rotation period should be ten times the image processing time of the digital camera as dictated by the frames per second and exposure time of the camera.

In various preferred embodiments of the methods according to the invention, the methods further comprise moving the optical fiber preform in the direction of its longitudinal axis, subsequent to obtaining a first plurality of images, and then acquiring a second plurality of images along the circumference of the preform at a different position along the length of the preform. The first, second and any additional pluralities of images are as described above except that they are captured at different location (circumferences) along the length of the preform. In other words, a first plurality of images may be obtained along circumference, and the preform may then be translationally moved along its longitudinal axis such that a line extending from the image capturing device to the pattern intersects the preform at a different circumference, and a second plurality of images may then be captured at a number of points along circumference, as the preform is again or continuously rotated.

Methods in accordance with the various embodiments of the invention further include determining at least one geometric property of an optical fiber preform from one or more plurality of images. A determination of a geometric property in accordance with the various method embodiments of the invention can be carried out by analysis of a first plurality of images at a single circumference of the preform, or multiple pluralities of images from various circumferences along the length of a preform can be analyzed and averaged to determine an overall or averaged property for the preform. For example, a single plurality of images at a single circumference can be analyzed to determine diameters, ovalities and eccentricity at one point along the length of a preform, or multiple pluralities may be analyzed to determine the average value of such properties for the entire preform. Overall preform bow requires multiple pluralities of images to be analyzed.

Figure 4A:
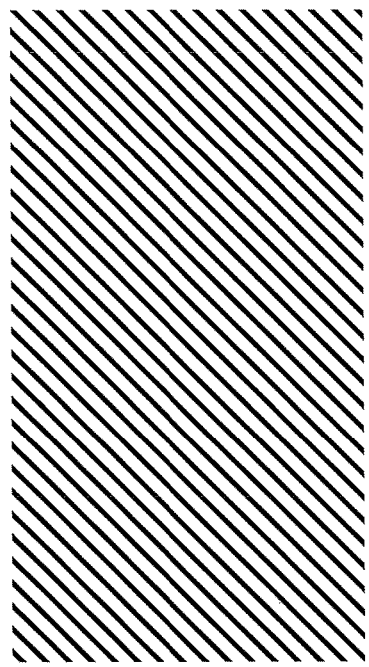
FIG. 4a is a graphical representation of a two-dimensional pattern suitable for use in accordance with an embodiment of the invention.
Figure 4B:
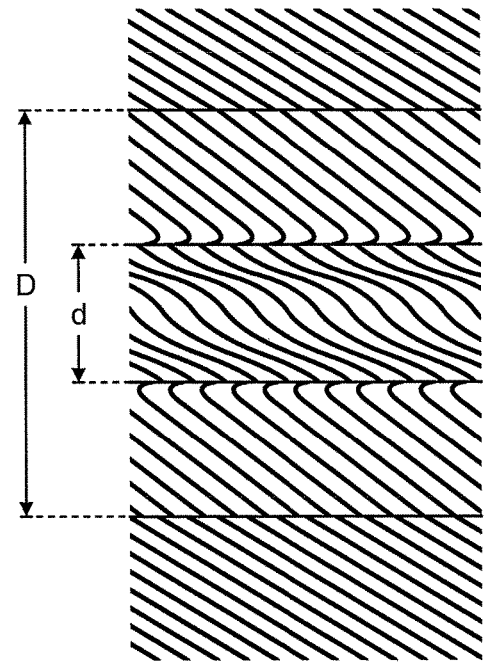
FIG. 4b is a representation of the pattern of FIG. 4a when viewed through an optical fiber preform.

In accordance with the various method embodiments of the invention, the determination of a geometric property is carried out by analysis to detect edge locations between the core and the cladding of an optical fiber preform. Such analyses are carried out by evaluating edge perturbations in the acquired images. For example, referring to FIG. 4a, a two-dimensional pattern suitable for use in a method according to the invention is shown. FIG. 4b is an image of the pattern shown in FIG. 4a, as viewed through an optical fiber preform. The "D" and "d" notations in FIG. 4b refer to the cladding layer diameter and core diameter, respectively, of the core rod through which the image was acquired. Thus, the disruption in the pattern lines resulting from changes in refractive index correspond to the edges of the core and clad diameter, and are referred to herein as "edge perturbations." The outer diameter of the entire preform is detected by the change in the pattern due to refraction of light at the preform edges.

Inspection of the edge perturbations to determine edge location can thus provide indications of the diameters of the core and cladding. Inspection of the edge perturbations to determine edge location at various different angular rotations along a single circumference, when compared to one another, can provide a determination of ovality and eccentricity. Determination of these properties at various different points along the length of a preform can provide averaged properties for the entire preform. Preform bow can be determined by comparing the absolute edge positions at different axial locations which can preferably be carried out in conjunction with a device for detecting angular position of the preform relative to a designated starting position as described herein.

Figure 5:
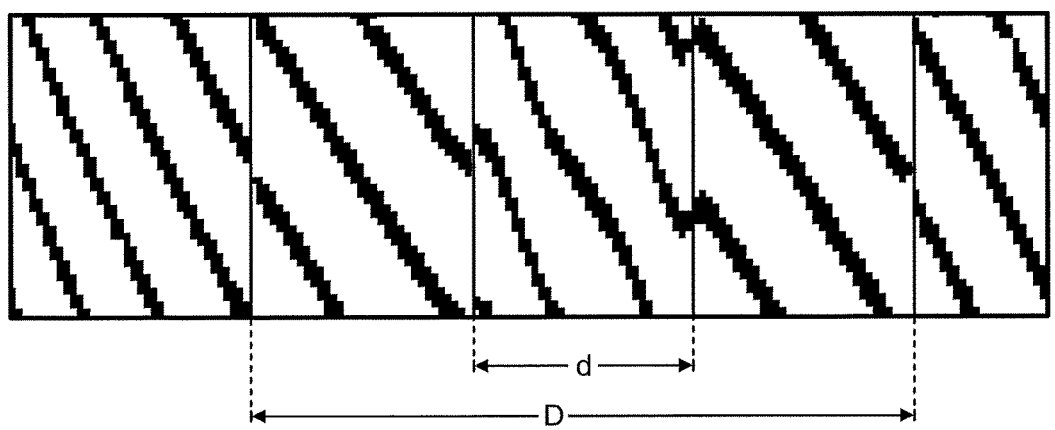
FIG. 5 is a magnified representation of a two-dimensional pattern in accordance with an embodiment of the invention showing pixilation employed in analysis in accordance with an embodiment of the invention.

In various preferred embodiments of the methods according to the invention, improved accuracy and precision of geometric property determination can be provided. In such various preferred embodiments, image analysis can be performed to provide more accurate and precise edge determination. For example, referring to FIG. 5, where a digital camera is used as the image capturing device, each image acquired can be analyzed at the individual pixel level, wherein edge perturbations at the outer diameter "D" and core diameter "d" are digitized.

Pixel analysis in accordance with various preferred embodiments of the invention can include standard deviation filtering, and image projection averaging. In various embodiments, pixel analysis can further include image erosion noise reduction carried out prior to standard deviation filtering and image projection averaging. Image erosion noise reduction includes elimination of high intensity pixels not surrounded by other high intensity pixels. Moreover, where a transition boundary has a large difference in indices of refraction, such as at the air/glass boundary of the overall preform outer diameter, magnification compensation can be performed to improve analytical results.

Standard deviation filtering includes replacing each pixel in an image with the standard deviation for that pixel relative to its environment. The filtering includes two steps. The first step is the calculation of standard deviations for subsets of three pixels along pixel rows. The second step calculates standard deviations for subsets of three pixels along pixel columns. The original image is replaced by the image filtered with the standard deviation algorithm for subsequent steps.

Image projection averaging can be used to average out separation edges between lines in the pattern so that only true distortions are enhanced. The image is projected along the edge direction using a Radon transform to provide the averaging effect.

Edge position detection for the core of a preform can be affected by the refractive effect of the outer layers (magnification effect) and the air interface. The magnification effect of the outer layers can be calculated by simulation of the optical system using optical ray tracing, where the refractive index of the outer layer cladding is known.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

What is claimed is:

1. A method comprising:
providing an optical fiber preform having a longitudinal axis, an outer diameter and a circumference, the optical fiber preform comprising at least two cylindrical layers of glass having different indices of refraction;
providing a two-dimensional pattern having a length parallel to the longitudinal axis of the optical fiber preform and a width greater than the outer diameter of the optical fiber preform;
providing an image capturing device disposed such that the optical fiber preform is aligned between the two-dimensional pattern and the image capturing device, the two-dimensional pattern comprising a plurality of straight lines extending across and beyond the outer diameter of the optical fiber preform in each direction when viewed from the image capturing device;
rotating the optical fiber preform about its longitudinal axis and acquiring a first plurality of images of the two-dimensional pattern viewed through the optical fiber preform at at least two different points along the circumference of the optical fiber preform; and
determining at least one geometric property of the optical fiber preform from the first plurality of images.

2. The method according to claim 1, wherein the two-dimensional pattern is illuminated.

3. The method according to claim 1, wherein the two-dimensional pattern is periodic in a lengthwise direction.

4. The method according to claim 1, wherein the two-dimensional pattern comprises alternating lines of contrasting brightness.

5. The method according to claim 1, wherein the two-dimensional pattern comprises alternating dark and bright lines, arranged periodically, and positioned at a non-perpendicular angle relative to the longitudinal axis of the optical fiber preform.

6. The method according to claim 5, wherein the non-perpendicular angle is about 40° to about 50°.

7. The method according to claim 6, wherein the two-dimensional pattern is illuminated.

8. The method according to claim 1, wherein the image capturing device comprises a digital camera.

9. The method according to claim 8, wherein the two-dimensional pattern comprises alternating dark and bright lines, arranged periodically, and positioned at a non-perpendicular angle relative to the longitudinal axis of the optical fiber preform, wherein the two-dimensional pattern is illuminated, wherein the alternating dark and bright lines each have a thickness, and wherein the thickness of the imaged lines at a detection plane of the digital camera is at least equal to a width of two pixels of the digital camera.

10. The method according to claim 1, wherein the first plurality of images comprises images of the two-dimensional pattern viewed through the optical fiber preform at at least five different points along the circumference of the optical fiber preform.

11. The method according to claim 1, wherein the first plurality of images comprises images of the two-dimensional pattern viewed through the optical fiber preform at at least ten different points along the circumference of the optical fiber preform.

12. The method according to claim 1, further comprising: moving the optical fiber preform in the direction of its longitudinal axis; rotating the optical fiber preform about its longitudinal axis and acquiring a second plurality of images of the two-dimensional pattern viewed through the optical fiber preform at at least two different points along the circumference of the optical fiber preform at a different location along its length than the first plurality of images; and determining at least one geometric property of the optical fiber preform from the second plurality of images or a combination of the first plurality and second plurality of images.

13. The method according to claim 1, wherein determining at least one geometric property of the optical fiber preform comprises identifying at least one value selected from the diameter, ovality and eccentricity of each of the at least two cylindrical layers.

14. The method according to claim 13, wherein identifying the at least one value comprises evaluating perturbations of the two-dimensional pattern in the plurality of images to determine relative spatial position of an edge between the at least two cylindrical layers.

15. The method according to claim 14, wherein the image capturing device is a digital camera, and wherein evaluating the perturbations of the two-dimensional pattern in the plurality of images to determine the relative spatial position of the edge comprises standard deviation filtering and image projection averaging.

16. The method according to claim 15, wherein evaluating the perturbations of the two-dimensional pattern in the plurality of images to determine the relative spatial position of the edge further comprises at least one pixel manipulation selected from the group consisting of image erosion noise reduction and magnification compensation.

17. The method according to claim 15, wherein the two-dimensional pattern comprises alternating dark and bright lines, arranged periodically, and positioned at a non-perpendicular angle relative to the longitudinal axis of the optical fiber preform, wherein the two-dimensional pattern is illuminated, wherein the alternating dark and bright lines each have a thickness, and wherein the thickness of the imaged lines at a detection plane of the digital camera is at least equal to a width of two pixels of the digital camera.

18. The method according to claim 13, wherein the image capturing device is a digital camera, wherein the two-dimensional pattern comprises alternating dark and bright lines, arranged periodically, and positioned at a non-perpendicular angle relative to the longitudinal axis of the optical fiber preform, wherein the two-dimensional pattern is illuminated, wherein the alternating dark and bright lines each have a thickness, and wherein the thickness of the imaged lines at a detection plane of the digital camera is at least equal to a width of two pixels of the digital camera;
further comprising moving the optical fiber preform in the direction of its longitudinal axis; rotating the optical fiber preform about its longitudinal axis and acquiring a second plurality of images of the two-dimensional pattern viewed through the optical fiber preform at at least two different points along the circumference of the optical fiber preform at a different location along its length than the first plurality of images;
wherein identifying the at least one value comprises evaluating perturbations of the two-dimensional pattern in the first plurality of images and second plurality of images to determine relative spatial position of an edge between the at least two cylindrical layers at two different positions along the longitudinal axis of the optical fiber preform; and wherein evaluating the perturbations of the two-dimensional pattern in each of the first plurality of images and the second plurality of images to determine the relative spatial position of the edge comprises standard deviation filtering and image projection averaging.

19. A method comprising:
providing an optical fiber preform having a longitudinal axis, an outer diameter, a circumference, and comprising at least two cylindrical layers of glass having different indices of refraction;
providing a two-dimensional pattern having a length parallel to the longitudinal axis of the optical fiber preform and a width greater than the outer diameter of the optical fiber preform, wherein the two-dimensional pattern comprises alternating dark and bright straight lines, arranged periodically, and positioned at a non-perpendicular angle relative to the longitudinal axis of the optical fiber preform, wherein the two-dimensional pattern is illuminated, wherein the alternating dark and bright lines each have a thickness;
providing a digital camera disposed such that the optical fiber preform is aligned between the two-dimensional pattern and the digital camera, wherein the thickness of each line of the two-dimensional pattern is at least equal to a width of two pixels of the digital camera, the alternating dark and bright straight lines extending across and beyond the outer diameter of the optical fiber preform in each direction when viewed from the digital camera;
rotating the optical fiber preform about its longitudinal axis and acquiring a first plurality of images of the two-dimensional pattern viewed through the optical fiber preform at at least ten different points along the circumference of the optical fiber preform;
moving the optical fiber preform in the direction of its longitudinal axis, and rotating the optical fiber preform about its longitudinal axis and acquiring a second plurality of images of the two-dimensional pattern viewed through the optical fiber preform at at least ten different points along the circumference of the optical fiber preform at a different location along its length than the first plurality of images; and
determining the diameter, ovality and eccentricity of each of the at least two cylindrical layers of the optical fiber preform from the first plurality and second plurality of images, wherein the determination comprises evaluating perturbations of the two-dimensional pattern in the first plurality of images and second plurality of images to determine relative spatial position of an edge between the at least two cylindrical layers at two different positions along the longitudinal axis of the optical fiber preform; and wherein evaluating the perturbations of the two-dimensional pattern in each of the first plurality of images and the second plurality of images to determine the relative spatial position of the edge comprises an analysis of image pixels comprising image erosion noise reduction, standard deviation filtering, image projection averaging and magnification compensation.

20. An apparatus for determining a geometric property of an optical fiber preform, the optical fiber preform having a longitudinal axis and an outer diameter, the optical fiber preform comprising at least two cylindrical layers of glass having different indices of refraction, the apparatus comprising:

an image capturing device;
a two-dimensional pattern having a length parallel to the longitudinal axis of the optical fiber preform and a width greater than the outer diameter of the optical fiber preform, the two-dimensional pattern comprising a plurality of straight lines;
a support configured to position the optical fiber preform in alignment between the image capturing device and the two-dimensional pattern, such that the two dimensional pattern extends length-wise in the direction of the longitudinal axis of the optical fiber preform and the plurality of straight lines extend across and beyond the outer diameter of the optical fiber preform in each direction when viewed from the image capturing device; and
a driver configured to rotate the optical fiber preform about its longitudinal axis in the support.

* * * * *